United States Patent [19]

Norman

[11] Patent Number: 5,041,225

[45] Date of Patent: Aug. 20, 1991

[54] HYDROPHILIC SEMI-PERMEABLE PTFE MEMBRANES AND THEIR MANUFACTURE

[76] Inventor: Eddie Norman, 'Forth View' Hawkcraig Point, Aberdour, Fife, Great Britain

[21] Appl. No.: 550,843

[22] Filed: Jul. 10, 1990

[30] Foreign Application Priority Data

Jul. 12, 1989 [GB] United Kingdom ............... 8915974

[51] Int. Cl.$^5$ ............................................. B01D 71/26
[52] U.S. Cl. ................................. 210/500.36; 55/158; 264/48
[58] Field of Search ............... 55/16, 158; 210/500.21, 210/500.22, 500.27, 500.36; 264/41, 45.1, 48, DIG. 48, DIG. 62

[56] References Cited

U.S. PATENT DOCUMENTS 4,318,714 3/1982 Kimura et al. ..................... 55/16

Primary Examiner—Frank Sever
Attorney, Agent, or Firm—Gary A. Samuels

[57] ABSTRACT

A hydrophilic, semipermeable membrane comprises a microporous PTFE membrane having the internal and external surfaces of the membrane structure coated by a complex formed by the combination of a hydrophilic polymer which adheres to the membrane structure and a complexing agent, the complex rendering the microporous PTFE membrane substantially hydrophilic and protein affinitive. The preferred hydrophilic polymariz/polyvinyl alcohol, and the complexing agent is preferably a dibasic inorganic acid, such as boric acid, or a salt thereof. Such hydrophilic, semipermeable membranes are particularly suitable for protecting the target area of a body fluid diagonistic test strip, and a cell culture support members. Methods of forming the membranes are also described.

11 Claims, 1 Drawing Sheet

HYDROPHILIC SEMI-PERMEABLE PTFE MEMBRANES AND THEIR MANUFACTURE

FIELD OF THE INVENTION

The invention relates to hydrophilic, semi-permeable membranes of PTFE (polytetrafluoroethylene) and their manufacture, and is particularly concerned with such membranes suitable for use in body fluid diagnostic test strips and as cell culture support members.

BACKGROUND OF THE INVENTION

Diagnostic devices are known which are able to give a quick, direct reading analysis of a blood or other body fluid sample for its content of a specific substance, such as sugar, alcohol, cholesterol, drugs, etc. These devices make use of a test strip carrying a composition (usually a conductive enzyme composition) which, when wetted by the body fluid sample, reacts electrochemically with the predetermined substance to be detected in the sample to provide an electrical signal which is measured and analysed by an electronic detector part of the device and displayed as a calibrated read-out. Test strips are also known in which the active composition is designed to change colour according to the content of the substance to be detected in the sample. In some cases the test strip may be dipped directly into the fluid sample to be tested, but generally it is more usual to apply a droplet of the sample onto a designated target area of the strip.

These devices are generally quite accurate if used correctly and under ideal conditions, but can all too easily give a false reading. The most common causes of error are excessive wetting of the test strip leading to electrode flooding, and excessive evaporation from the sample during the test reaction time (which may take up to 60 seconds) which effectively increases the measured concentration of the detected substance. In some cases the presence of red blood cells or other protein cells can also affect the reaction and hence the accuracy of the test result.

It has therefore been proposed to cover the target area of the test strip by a semi-permeable membrane so that the fluid sample is applied to the target area in a controlled manner through the membrane, the membrane also acting to allow efficient oxygen permeation through the membrane to the target area while controlling the rate of evaporation from the sample applied to the target area.

Microporous PTFE membranes, such as GORE-TEX (R.T.M.) membranes manufactured in accordance with British Patent No. 1355373 of W. L. Gore & Associates Inc., are potentially very suitable for this purpose because of their high porosity and relatively narrow pore size distribution, and also because they are strong, chemically inert and steam sterilizable. Unfortunately, they cannot be used in their natural state because they are highly hydrophobic, thus inhibiting the transmission of aqueous fluids, and they are also protein repellent which, in the case of blood samples, can lead to premature coagulation and consequent blinding of the membrane.

Several treatments are commonly used for inducing hydrophilic activity in naturally hydrophobic polymeric membranes, but generally these use detergent surfactants based on metal soaps, fatty acid esters, ammonium salts or amines etc., and are unsuitable for membranes intended for use on diagnostic test strips as described above.

It is also known that a porous PTFE membrane can be rendered hydrophilic by impregnating it with a hydrophilic, water soluble polymer, such as polyvinylacohol, and then fixing the polymer by rendering it water insoluble by cross-linking. We have found that such hydrophilic polymer coatings applied to the pores of a microporous PTFE membrane can also be fixed by using a suitable complexing agent which forms a complex with the polymer, and that the complex exhibits good protein bonding characteristics in the presence of water.

SUMMARY OF THE INVENTION

According to the invention, therefore, there is provided a hydrophilic, semi-permeable membrane comprising a microporous PTFE membrane having the internal and external surfaces of the membrane structure coated with a complex formed by the combination of a hydrophilic polymer which adheres to the membrane structure and a complexing agent, the complex rendering the microporous PTFE membrane substantially hydrophilic and protein affinitive.

DETAILED DESCRIPTION OF THE INVENTION

Figure 1:
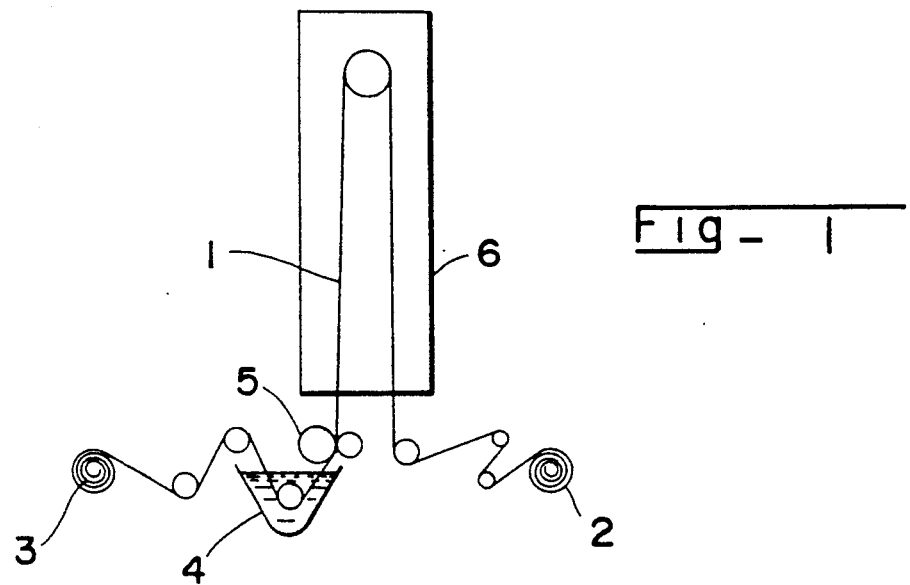
FIG. 1 is a schematic diagram illustrating a single stage process for producing a semi-permeable membrane in accordance with the invention.

Preferably the hydrophilic polymer is an oxygen containing, water soluble polymer, such as polyvinyl alcohol, polyvinyl acetate, or polyvinyl pyrollidene. The polymer may also be a closely related ester derivative of such polymers or a copolymer or mixture thereof. Such polymers are generally soluble in alcohol as well as in water, which facilitates their application to the PTFE membrane structure, and also exhibit good polar bonding characteristics. In addition, they are generally inert with respect to blood and other body fluids. Indeed, it has been known to use polyvinyl alcohol as a blood plasma substitute.

The preferred polymer for use in the present invention is a polyvinyl alcohol which is at least 80% hydrolyzed (preferably at least 86% hydrolyzed), and which has a molecular weight of less than 50000.

The complexing agent may be an ionic buffer salt or acid, and is preferably a dibasic inorganic acid or salt thereof. Examples of suitable complexing agents are metal salts such as sodium chloride, potassium chloride, ammonium chloride, sodium borate, and sodium salicylanilide, boric acid, vanadic acid, gallic acid, and congo red.

The preferred complexing agent is boric acid, sodium borate, or sodium chloride.

The complexing mechanism is not fully understood, but it appears that the complexing agent engages in polar bonding with available oxygen or hydroxyl groups of the hydrophilic polymer to produce the complex. In the case of the preferred hydrophilic polymer (polyvinyl alcohol) and complexing agent (boric acid) a bisdiol complex is formed as follows:

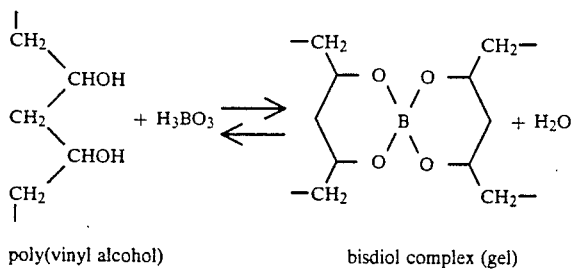

poly(vinyl alcohol)  bisdiol complex (gel)

Such complexing substantially reduces the subsequent water resolubility of the hydrophilic polymer based coating on the surfaces of the microporous PTFE membrane structure, and when reactivated by contact with an aqueous solution forms a hydrogel exhibiting strong protein binding characteristics. This is particularly evident with complexes formed by using boric acid or a salt thereof as the complexing agent, possibly due to chelation between the borate or other boron anion complex and protein molecules such as red blood cells.

Such a semi-permeable membrane is thus particularly suitable for use in covering the target area of a body fluid diagnostic test strip as described earlier, it allows rapid but controlled penetration of the fluid sample to the tazget area of the test strip, while also substantially reducing evaporation and permitting oxygen to reach the reaction as required. Also, it is highly efficient at separating red blood cells and other protein cells from the fluid which is required to pass to the target area, even when the pore size of the membrane is greater than the size of the cells, the cells adhering readily to the complex coating the membrane structure. In addition the coated membrane is substantially inert with respect to the test reaction and to blood and other body fluids, and is generally slightly acidic, although this can be controlled as desired by selection and adjustment of the complexing agent or by additional buffering.

These properties also render the semi-permeable membranes in accordance with the invention suitable for use in cell culture applications, such as the formation of layers of endothelial cells for use in transendothelial chemotactic studies. In such cases the membrane provides an ideal support for the growth of the endothelial cells which readily attach to the protein affinitive complex coating the membrane structure.

The thickness of the membrane will usually be from 0.01 to 0.2 mm, and the average jure size of the membrane may be from 0.2 to 15 microns as defined by the bubble point method ASTM. F316-70.

The membrane may be used on its own or, if preferred, may be laminated to a non-woven fabric support layer.

This support layer may have a thickness from 0.1 to 0.75 mm and may be formed for example from polyester, polypropylene, nylon or regenerated cellulose fibres.

According to a further aspect of the invention, a method of producing a semi-permeable membrane in accordance with the invention comprises subjecting the microporous PTFE membrane to a treatment solution containing the hydrophilic polymer, the complexing agent, and a solvent in which the hydrophilic polymer and the complexing agent are soluble and which is capable of wetting the PTFE membrane, so that the pore structure of the membrane is substantially completely impregnated by the solution, and drying the membrane to evaporate the solvent and thereby leave a complex formed by a combination of the hydrophilic polymer and the complexing agent coated on the internal and external surfaces of the membrane.

Alternatively, the method can be carried out in two stages, with the microporous PTFE membrane first being subjected to a solution of the hydrophilic polymer to coat the membrane structure with the polymer, and then to a solution of the complexing agent to form a complex with the hydrophilic polymer coating on the membrane structure.

The solvent is preferably an aliphatic alcohol or a ketone, and may be mixed with water so that the water is present in an amount which is from 20% to 60% by volume of the water and solvent mixture. Suitable solvents are ethanol, methanol, propanol, butanol, and acetone.

The hydrophilic polymer may be present in the treatment solution in an amount which is from 0.2% to 5%, preferably 0.2% to 2%, weight by volume of the solvent or solvent and water mixture.

The complexing agent is preferably present in the solution in an amount which is less than 10% weight by volume of the solution.

The treatment solution may also contain a surfactant to act as a dispersion agent.

Preferably the membrane is impregnated by immersion in the treatment solution, and the treatment may be carried out continuously.

Two examples of a process for producing a semipermeable membrane in accordance with the invention will now be described with reference to the accompanying drawings.

In the process illustrated in FIG. 1, a continuous web 1 of the microporous PTFE membrane to be treated is drawn by a take-up roll 2 from a feed roll 3 through an impregnation bath 4, a pair of squeeze rollers 5 for removing excess liquid from the web, and then upwards and downwards through a vertical drying oven 6, the web 1 being guided by suitable guide rollers as necessary. Heated air is supplied at about 60°0 C. to the bottom of the drying oven 6, and air and gases evaporated from the impregnated web 1 are exhausted from the upper end.

The treatment solution in the impregnation bath 4 is made from: 2500 ml water.,
250 ml polyvinyl alcohol No.2 (a 20% solution in water of an 88% hydrolysed polyvinyl alcohol having a molecular weight less than 30000),
5 ml Fluorad 340 (a surfactant dispersion agent obtained from the Minnesota Mining and Manufacturing Company);
200 grams boric acid;
2500 ml isopropanol.

The solution is made by first heating the polyvinyl alcohol with the water to boiling and allowing the PVA to dissolve completely. When the solution has cooled to below 50° C., the remaining constituents are added and stirred in thoroughly to form a treatment solution containing approximately 1% polyvinyl alcohol W/V and approximately 4% boric acid W/V.

In operation, the web 1 is fully impregnated by the treatment solution as it is drawn through the bath 4, the presence of the alcohol in the solution serving to wetout the PTFE membrane so that the solution can penetrate fully into the porous structure of the membrane.

Typically the web 1 may be drawn through the bath 4 and the drying oven 6 at a rate of about 2 metres per minute. Upon drying, alcohol and water are evaporated from the impregnated membrane,. leaving a thin coating of a bisdiol complex formed from the PVA and boric acid firmly adhered to the surfaces of the microporous structure without significantly reducing the porosity of the membrane.

Figure 2:
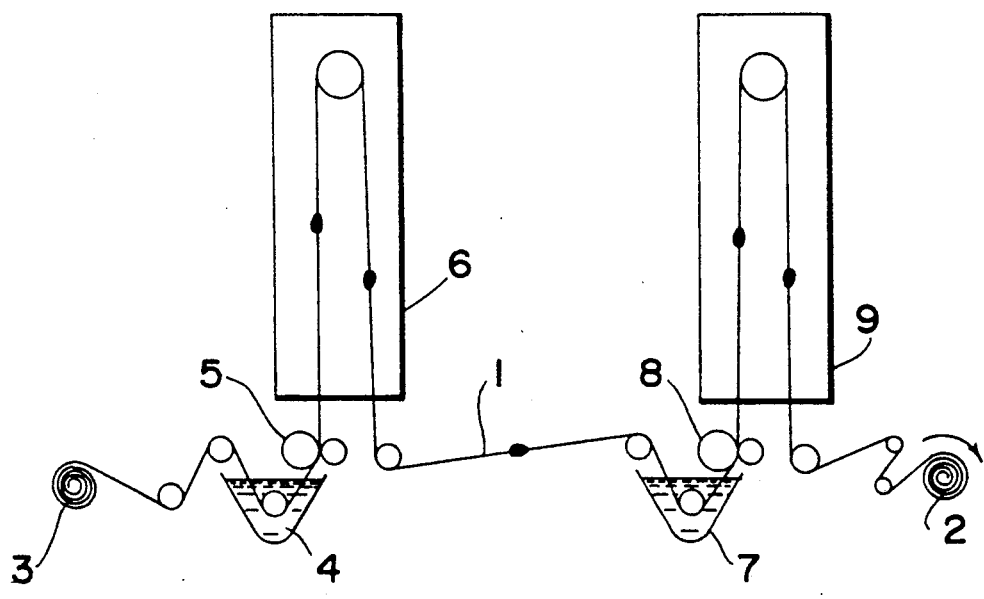
FIG. 2 is a schematic diagram illustrating a two-stage process for producing a semi-permeable membrane in accordance with the invention.

In the two-stage process shown in FIG. 2, the apparatus is similar to that shown in FIG. 1 except that following the drying oven 6 the web 1 is drawn through a further impregnation bath 7, squeeze rollers 8, and drying oven 9 before being wound onto the take-up roll 2. In this case the impregnation bath 4 contains a treatment solution made from:
2500 ml water;
200 ml polyvinyl alcohol No. 2;
5 ml Aerosol OT-75 (a surfactant obtained from the Cyanamid Company);
2500 ml isopropanol.

The impregnation bath 7 contains a solution made from:
2500 ml water;
200 grams sodium chloride With this arrangement the membrane web 1 is first impregnated by the solution in the bath 4 and dried to produce a thin coating of the polyvinyl alcohol on the surfaces of the microporous membrane structure, and is then impregnated by the solution in the bath 7 to bring the NaCl complexing agent into contact with the PVA coating to form a complex therewith which substantially reduces the resolubility of the subsequently dried coating.

In these examples the microporous PTFE membrane is a Gore-Tex (RTM) membrane having a pore size of from 10 to 15 microns, and is backed by a non-woven polyester fabric support.

I claim:

1. A hydrophilic, semi-permeable membrane comprising a porous polytetrafluoroethylene membrane having the internal and external surfaces of the membrane structure coated by a complex formed by the combination of a hydrophilic oxygen containing, water soluble polymer which adheres to the membrane structure and a complexing agent that is an ionic buffer salt or acid, the complex rendering the porous PTFE membrane substantially hydrophilic and protein affinitive.

2. A semi-permeable membrane according to claim 1, in which the hydrophilic polymer is polyvinyl alcohol, polyvinyl acetate, polyvinyl pyrollidone, or a copolymer or mixture thereof.

3. A semi-permeable membrane according to claim 2, in which the hydrophilic polymer is a polyvinyl alcohol which is at least 80% hydrolysed and which has a molecular weight of less than 5000.

4. A semi-permeable membrane according to claim 1, in which the complexing agent is a dibasic inorganic acid or a salt thereof.

5. A semi-permeable membrane according to claim 4, in which the complexing agent is boric acid or sodium borate.

6. A semi-permeable membrane according to claim 1 in which the porous PTFE membrane is laminated to a non-woven fabric support layer.

7. A semi-permeable membrane according to claim 6 in which the non-woven fabric support layer is formed of polyester, polypropylene, nylon, or regenerated cellulose fibres.

8. A method of producing a semi-permeable membrane comprising subjecting a porous PTFE membrane to a treatment solution containing a hydrophilic oxygen containing, water soluble polymer, a complexing agent that is an ionic buffer salt or acid, and a solvent in which the hydrophilic polymer and the complexing agent are soluble and which is capable of wetting the PTFE membrane, so that the pore structure of the membrane is substantially completely impregnated by said solution, and drying the membrane to evaporate the solvent and thereby leave a complex formed by a combination of the hydrophilic polymer and the complexing agent coated on the internal and external surfaces of the membrane.

9. A method of producing a semi-permeable membrane comprising subjecting porous PTFE membrane to a treatment solution containing a hydrophilic oxygen containing, water soluble polymer and a solvent for the hydrophilic polymer which is capable of wetting the PTFE membrane so that the pore structure of the membrane is substantially completely impregnated by said solution drying the membrane to evaporate the solvent and thereby leave a coating of the hydrophilic polymer adhered to the internal and external surfaces of the membrane, then subjecting the treated membrane to a solution of a complexing agent that is an ionic buffer salt or acid so that the pore structure of the membrane is substantially completely impregnated thereby and the complexing agent combines with the hydrophilic polymer coating to form a complex, and drying the membrane.

10. A method according to claim 8 or claim 9 in which the solvent in the treatment solution is an aliphatic alcohol or a ketone.

11. A method according to claim 10 in which the solvent is ethanol, methanol, propanol, butanol, or acetone.

* * * * *